United States Patent
Douglas et al.

(10) Patent No.: US 10,864,043 B2
(45) Date of Patent: Dec. 15, 2020

(54) INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING

(71) Applicants: Kathleen M Douglas, Winter Park, FL (US); Robert E Douglas, Winter Park, FL (US)

(72) Inventors: Kathleen M Douglas, Winter Park, FL (US); Robert E Douglas, Winter Park, FL (US)

( * ) Notice: Subject to any disclaimer, the term of this patent is extended or adjusted under 35 U.S.C. 154(b) by 0 days.

(21) Appl. No.: 16/010,925

(22) Filed: Jun. 18, 2018

(65) Prior Publication Data

US 2019/0247121 A1 Aug. 15, 2019

Related U.S. Application Data

(60) Provisional application No. 62/628,527, filed on Feb. 9, 2018.

(51) Int. Cl.
*G06T 19/20* (2011.01)
*A61B 34/10* (2016.01)

(52) U.S. Cl.
CPC .............. *A61B 34/10* (2016.02); *G06T 19/20* (2013.01); *A61B 2034/102* (2016.02); *A61B 2034/104* (2016.02); *A61B 2034/105* (2016.02); *A61B 2034/108* (2016.02); *G06T 2219/004* (2013.01); *G06T 2219/2004* (2013.01); *G06T 2219/2012* (2013.01); *G06T 2219/2016* (2013.01); *G06T 2219/2021* (2013.01)

(58) Field of Classification Search
None
See application file for complete search history.

(56) References Cited

U.S. PATENT DOCUMENTS

| 2003/0016850 | A1* | 1/2003 | Kaufman | G06F 19/321 |
| | | | | 382/128 |
| 2013/0266198 | A1* | 10/2013 | Pereira | G06T 7/0012 |
| | | | | 382/131 |
| 2014/0359504 | A1* | 12/2014 | Kim | G06F 3/0488 |
| | | | | 715/768 |
| 2015/0227679 | A1* | 8/2015 | Kamer | G16B 5/00 |
| | | | | 703/11 |
| 2018/0310907 | A1* | 11/2018 | Zhang | A61B 6/5223 |
| 2018/0374276 | A1* | 12/2018 | Powers | G06T 19/20 |
| 2019/0333221 | A1* | 10/2019 | Nakagomi | G06T 5/50 |

\* cited by examiner

*Primary Examiner* — Yanna Wu

(57) ABSTRACT

An interactive placement of a digital representation of a surgical device or anatomic feature into a radiologic 3D medical image that contains a feature of interest is described. Integration of the digital representation of the surgical device or anatomic feature with the radiologic 3D medical image facilitates pre-operative surgical planning and surgical device selection. Location indicators, annotations, and registration markers may be overlaid on selected volume images.

16 Claims, 13 Drawing Sheets

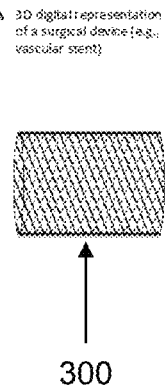

Fig. 3A

A. 3D digital representation of a surgical device (e.g., vascular stent)

300

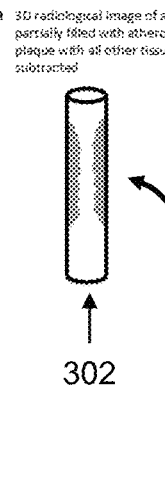

Fig. 3B

B. 3D radiological image of artery partially filled with atherosclerotic plaque with all other tissues subtracted

302

304

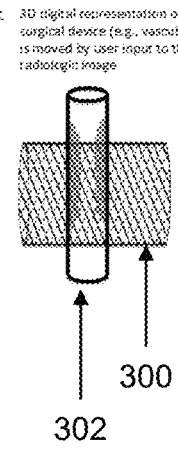

Fig. 3C

C. 3D digital representation of a surgical device (e.g., vascular stent) is moved by user input to the 3D radiologic image 300   302

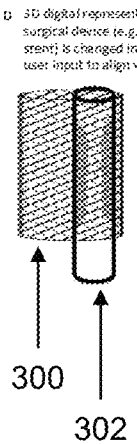

Fig. 3D

D. 3D digital representation of a surgical device (e.g., vascular stent) is changed in orientation by user input to align with the artery 300   302

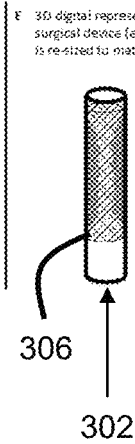

Fig. 3E

E. 3D digital representation of a surgical device (e.g., vascular stent) is re-sized to match with artery 306   302

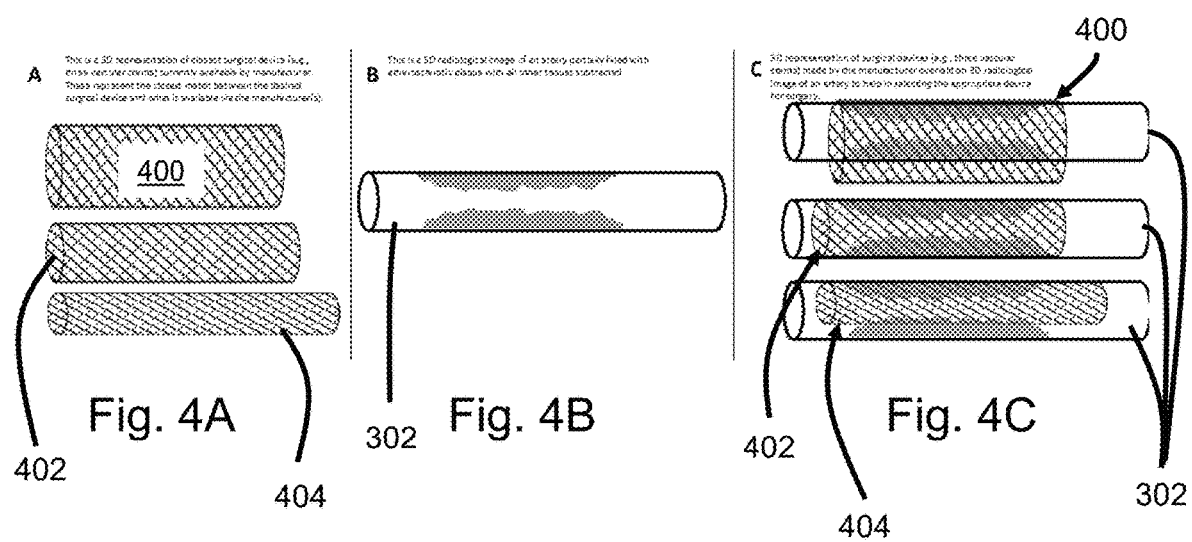

Description 504

Description 506

Fig. 6A
Fig. 6B
Fig. 6C
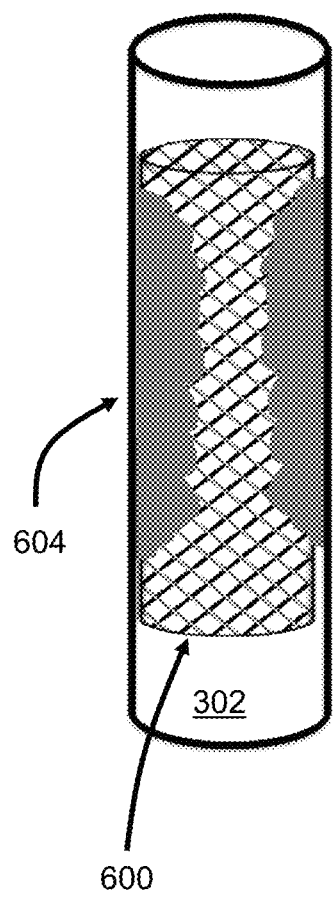
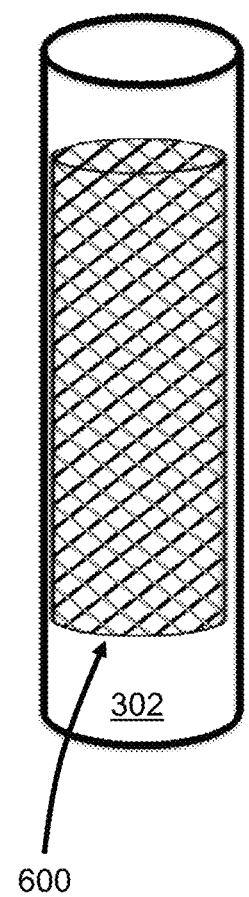
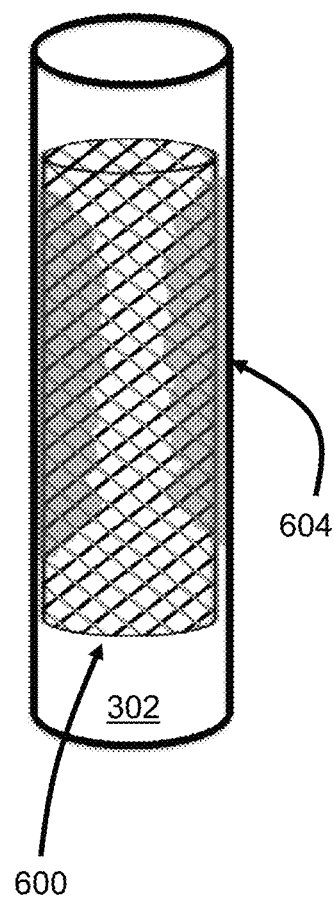

INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING

CROSS-REFERENCE TO RELATED APPLICATIONS

This application claims priority to U.S. Provisional Patent Application 62/628,527, titled A METHOD AND APPARATUS FOR INTERACTIVE PLACEMENT OF A DIGITAL REPRESENTATION OF A SURGICAL DEVICE INTO RADIOLOGIC IMAGES, filed Feb. 9, 2018, which is incorporated by reference.

TECHNICAL FIELD

Aspects of this disclosure are generally related to radiological imaging, and more particularly to surgical planning.

BACKGROUND

During an interventional radiologist's or surgeon's pre-operative planning phase prior to performing a surgery, the surgeon assesses the patient's age, gender, past medical history, past surgical history, medications, allergies, physical examination, and pre-operative imaging that is available. In addition, there is a review of equipment that is planned to be used during the operation. A wide variety of surgical equipment and interventional radiological equipment exists, and certain types of equipment may be available in various configurations, e.g. different materials, shapes, and sizes.

The current standard for surgeons to determine which piece of surgical equipment to use in performing an operation is a careful set of measurements on cross-sectional imaging datasets, such as computed tomography (CT) or magnetic resonance imaging (MRI). The surgeon uses these measurements to help plan specifically which equipment might be used during the operation. It is typical for the surgeon or interventional radiologist to request several similar pieces of surgical equipment so that if one piece doesn't have a suitable configuration, another piece in a suitable configuration is readily available for use.

Recently, techniques for 3D viewing of medical images have been described, such as U.S. Pat. No. 8,384,771. This process for transforming cross-sectional imaging data into true 3D viewing on an augmented reality or virtual reality headset with gaming controller has been further explored and is discussed in a recent review article by Douglas, D. B., Wilke, C. A., Gibson, J. D., Boone, J. M., Wintermark, M. Augmented Reality: Advances in Diagnostic Imaging. Multimodal Technologies and Interaction, 2017; 1(4):29. While there are significant improvements in the visualization capabilities with this technique, there are still limitations in the ability to perform pre-operative planning as explained below.

The first limitation is that it is inherently difficult to use 2D measurement tools to measure a 3D surgical object. The tools on standard radiology picture archiving and communication systems (PACS) and other similar workstations only provide linear or area measurements on cross-sectional imaging datasets. This limits the ability to pre-operatively select a surgical device which has a suitable length, width, and height.

The second limitation is that it is inherently difficult to precisely match the natural curvatures of the human body structure of interest (e.g., artery) with the natural curvature of the surgical equipment (e.g., stent). This limits the ability to pre-operatively select an appropriately shaped surgical device.

The third limitation is that it is inherently difficult to determine how multiple different human body structures and multiple surgical devices will all fit together in a pre-operative setting. This limits the ability to pre-operatively select the appropriate number, size and shape of the surgical devices when used in combination.

Consequently, there is a need for a system that enables the observer to optimally select suitable surgical devices and other equipment pre-operatively.

SUMMARY

All examples, aspects and features mentioned in this document can be combined in any technically possible way.

In accordance with an aspect, a method comprises: generating a digital 3D representation of at least one generic surgical device; responsive to a first input, moving the digital 3D representation of the generic surgical device relative to a digital 3D representation of an anatomic feature obtained from at least one medical image; responsive to a second input, aligning the digital 3D representation of the generic surgical device with the digital 3D representation of the anatomic feature; responsive to a third input, configuring the digital 3D representation of the generic surgical device based on the digital 3D representation of the anatomic feature by adjusting at least one of size, shape, and material properties, thereby generating a configured digital 3D representation of the generic surgical device; responsive to a fourth input, finding at least one real surgical device that is a closest match with the configured digital 3D representation of the generic surgical device; and responsive to a fifth input, generating a digital 3D representation of the at least one real surgical device presented with the digital 3D representation of the anatomic feature. In some implementations generating the digital 3D representation of at least one real surgical device (i.e., available from manufacturer) aligned with the digital 3D representation of the anatomic feature comprises generating a digital 3D representation of a plurality of real surgical devices, each aligned with a separate copy of the digital 3D representation of the anatomic feature. Some implementations comprise adjusting transparency of: the digital 3D representation of the generic surgical device; the digital 3D representation of the at least one real surgical device; and the digital 3D representation of the anatomic feature. Some implementations comprise adding annotations to the digital 3D representation of the at least one real surgical device aligned with the digital 3D representation of the anatomic feature. Some implementations comprise adding measurement markers to the digital 3D representation of the at least one real surgical device aligned with the digital 3D representation of the anatomic feature. Some implementations comprise adding location indicators that provide directional information to the digital 3D representation of the at least one real surgical device aligned with the digital 3D representation of the anatomic feature. Some implementations comprise adding false color to the digital 3D representation of the at least one real surgical device aligned with the digital 3D representation of the anatomic feature. Some implementations comprise adding reference lines to conventional cross-sectional imaging planes associated with the digital 3D representation of the at least one real surgical device aligned with the digital 3D representation of the anatomic feature.

In accordance with an aspect an apparatus comprises: an input/output (TO) device; and an image processor in communication with the IO device, the image processors comprising a program stored on computer-readable non-transitory media, the program comprising: instructions that generate a digital 3D representation of at least one generic surgical device on the IO device; instructions that move the digital 3D representation of the generic surgical device relative to a digital 3D representation of an anatomic feature obtained from at least one medical image; instructions that align the digital 3D representation of the generic surgical device with the digital 3D representation of the anatomic feature; instructions that configure the digital 3D representation of the generic surgical device based on the digital 3D representation of the anatomic feature by adjusting at least one of size, shape, and material properties, thereby generating a configured digital 3D representation of the generic surgical device; instructions that find at least one real surgical device that is a closest match with the configured digital 3D representation of the generic surgical device; and instructions that generate a digital 3D representation of the at least one real surgical device presented with the digital 3D representation of the anatomic feature. In some implementations the instructions that generate the digital 3D representation of the at least one real surgical device aligned with the digital 3D representation of the anatomic feature comprise instructions that generate a digital 3D representation of a plurality of real surgical devices, each aligned with a separate copy of the digital 3D representation of the anatomic feature. Some implementations comprise instructions that adjust transparency of: the digital 3D representation of the generic surgical device; the digital 3D representation of the at least one real surgical device; and the digital 3D representation of the anatomic feature. Some implementations comprise instructions that add annotations to the digital 3D representation of the at least one real surgical device aligned with the digital 3D representation of the anatomic feature. Some implementations comprise instructions that add measurement markers to the digital 3D representation of the at least one real surgical device aligned with the digital 3D representation of the anatomic feature. Some implementations comprise instructions that add location indicators that provide directional information to the digital 3D representation of the at least one real surgical device aligned with the digital 3D representation of the anatomic feature. Some implementations comprise instructions that add false color to the digital 3D representation of the at least one real surgical device aligned with the digital 3D representation of the anatomic feature. Some implementations comprise instructions that add reference lines to conventional cross-sectional imaging planes associated with the digital 3D representation of the at least one real surgical device aligned with the digital 3D representation of the anatomic feature.

In accordance with an aspect a method comprises: generating a digital 3D representation of a first anatomic feature obtained from a first medical image; generating a digital 3D representation of a second anatomic feature obtained from a second medical image; responsive to a first input, moving the digital 3D representation of the first anatomic feature relative to the digital 3D representation of the second anatomic feature; and responsive to a second input, aligning the digital 3D representation of the first anatomic feature with the digital 3D representation of the second anatomic feature. In some implementations aligning the digital 3D representation of the first anatomic feature with the digital 3D representation of the second anatomic feature comprises one of: virtually aligning a vein with a coronary artery; virtually aligning a first kidney with a second kidney; virtually aligning a first bone tissue with a second bone tissue; and virtually aligning a first fat tissue with a second fat tissue. Some implementations comprise adding reference lines to conventional cross-sectional imaging planes associated with the digital 3D representations of the first and second anatomic features. Some implementations comprise replacing voxels from the receiving 3D medical imaging dataset with the inputted 3D medical image, while other implementations comprise distorting voxels within the receiving 3D medical imaging dataset in order to accommodate the differing size/shape/orientation of the inputted 3D medical image.

In accordance with an aspect an apparatus comprises: an IO device; and an image processor in communication with the IO device, the image processors comprising a program stored on computer-readable non-transitory media, the program comprising: instructions that generate a digital 3D representation of a first anatomic feature obtained from a first medical image; instructions that generate a digital 3D representation of a second anatomic feature obtained from a second medical image; instructions that move the digital 3D representation of the first anatomic feature relative to the digital 3D representation of the second anatomic feature; and instructions that align the digital 3D representation of the first anatomic feature with the digital 3D representation of the second anatomic feature. In some implementations the instructions that align the digital 3D representation of the first anatomic feature with the digital 3D representation of the second anatomic feature cause on of the following: virtual alignment of a vein with a coronary artery; virtual alignment of a first kidney with a second kidney; virtual alignment of a first bone tissue with a second bone tissue; and virtual alignment of a first fat tissue with a second fat tissue. Some implementations comprise instructions that add reference lines to conventional cross-sectional imaging planes associated with the digital 3D representations of the first and second anatomic features. Some implementations comprise replacing voxels from the receiving 3D medical imaging dataset with the inputted 3D medical image, while other implementations comprise distorting voxels within the receiving 3D medical imaging dataset in order to accommodate the differing size/shape/orientation of the inputted 3D medical image.

In accordance with an aspect of this invention a method comprises: generating a digital 3D representation of a generic surgical device(s); responsive to a first input, moving the 3D digital representation of a generic surgical device along a desired course within a 3D medical image; responsive to a second input, aligning the 3D digital representation of a generic surgical device to the desired anatomic structure(s) within the 3D medical image(s); responsive to a third input, adjusting the size, shape and material properties of the 3D digital representation of a surgical device(s) to achieve optimal surgical outcome; responsive to a fourth input, determination of the optimum match(es) of the desired surgical device(s) with devices currently available by manufacturer(s); and responsive to a fifth input, replacing the generated 3D digital representation of a selected surgical device designed by user input with a 3D digital representation of a surgical device made by a manufacturer.

Because certain manufacturers use different shapes, sizes, and materials, a look-up process to determine a best match may be performed.

In some implementations, presenting the modified version of the selected digital representation of the surgical device comprises the trial of multiple 3D representations of a manufacturer's surgical devices of varying sizes to determine best match with the patient's unique anatomy.

In some implementations, presenting the modified version of the selected digital representation of the surgical device comprises adjusting the transparency of both the 3D digital representation of a surgical device and the 3D medical image to achieve optimal visualization.

In some implementations, presenting the modified version of the selected digital representation of the surgical device comprises adding annotations to the digital representation of the surgical device to denote important observations, such as its selection or precise placement.

In some implementations, presenting the modified version of the selected digital representation of the surgical device comprises adding measurement metrics, such as digital ruler, area, or volume to at least one edge, surface or side.

In some implementations, presenting the modified version of the selected digital representation of the surgical device comprises adding measurement metrics, such as quantitative evaluation to assess adequacy of placement of hardware pre-operatively.

In some implementations, presenting the modified version of the selected digital representation of the surgical device comprises presenting inputted location indicators such as within the digital representation of the surgical device, within the 3D medical image.

In some implementations, presenting the modified version of the selected digital representation of the surgical device comprises presenting the images along with reference lines to conventional cross-sectional imaging planes, such as axial, sagittal, coronal or oblique reformats.

In some implementations, presenting the modified version of the selected digital representation of the surgical device comprises a variety of surgical devices that are permanently or temporarily placed into the body including: vascular stent(s); orthopedic hardware; cardiac device(s); plastic surgical implant(s) or other devices used for surgery on the brain, head, neck, face, chest, abdomen, pelvis or extremities.

In accordance with an aspect of this invention a method comprises: generating a digital 3D medical image of two or more body tissues in two or more separate volumes; responsive to a first input, moving the 3D image of one body tissue on the first volume along a desired course onto the additional body tissue(s); and responsive to a second input, aligning the 3D digital representation of the one body tissue from the first 3D medical image to the subsequent anatomic structure(s) within the 3D medical image(s). In certain procedures, e.g. transplants, the body tissue is moved from one person to another (e.g., kidney transplant, liver transplant, etc.).

In some implementations presenting the modified version of a digital 3D medical image of body tissues from more than one volume, the tissues include, but are not limited to: vein moved to coronary artery as is done in performing a coronary artery bypass graft; transplant of a kidney from one patient to another; bone graft from one area of the body to another; fat transfer from one part of the body to another.

In some implementations presenting the modified version of a digital 3D medical image of body tissues from more than one volume comprises presenting the images along with reference lines to conventional cross-sectional imaging planes, such as axial, sagittal, coronal or oblique reformats.

Note that throughout this patent we refer to the insertion into another scan; however, it should be noted that the insertion could be into a new 3D database or virtual 3D medical imaging working space.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 3A, 3B, 3C, 3D, and 3E collectively illustrate configuring the generic surgical device to aid in selection of the real surgical device.

FIGS. 4A, 4B, and 4C collectively illustrate integrating representations of real surgical devices with the 3D medical image to aid in selection of a preferred real surgical device.

FIGS. 6A, 6B, and 6C collectively illustrate adjusting the transparency of a surgical device and/or 3D medical images.

DETAILED DESCRIPTION

Some aspects, features and implementations described herein may include machines such as computers, electronic components, radiological components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1:
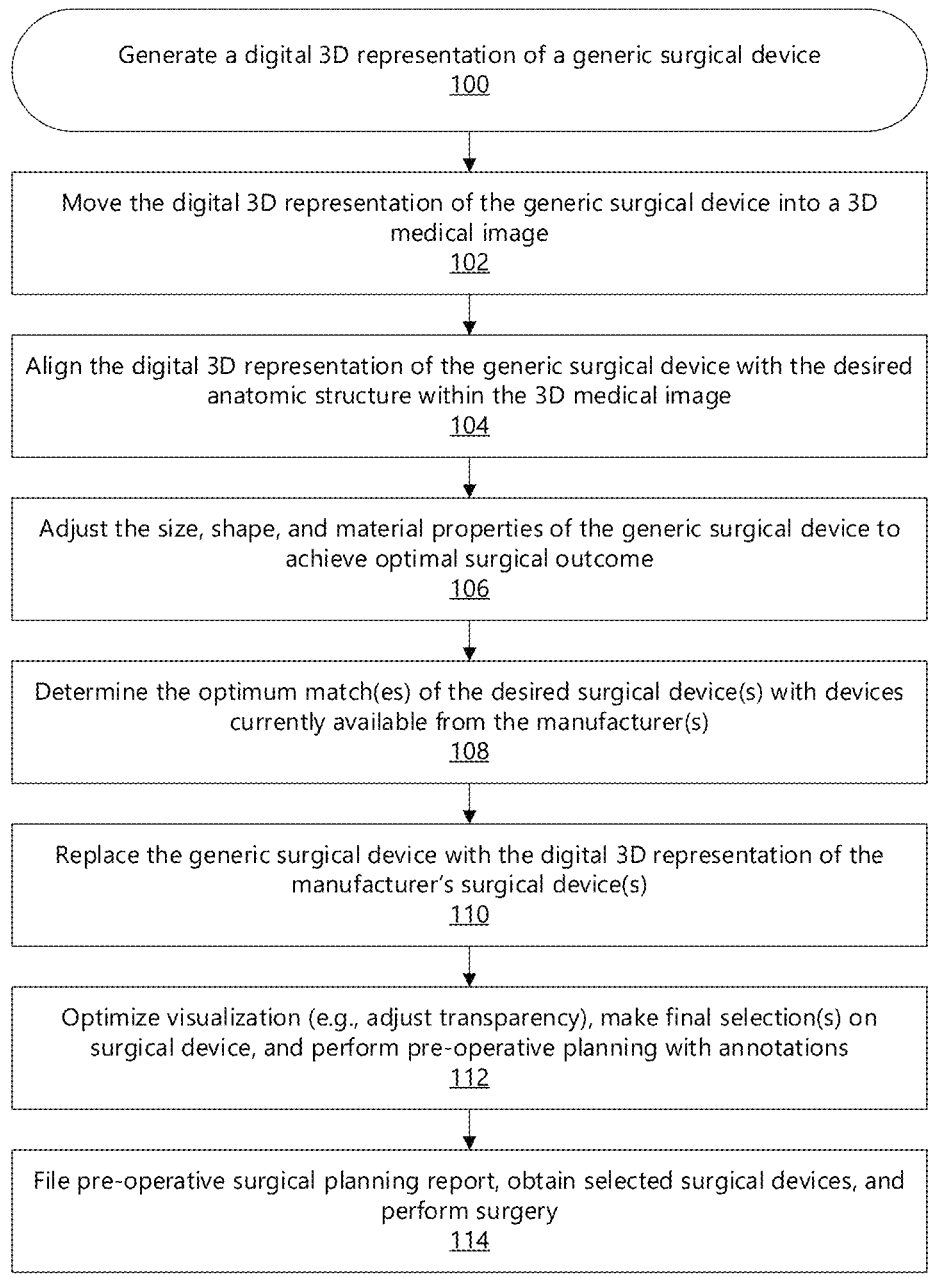
FIG. 1 is a flow diagram that illustrates a pre-operative planning process that includes generating a digital 3D representation of a generic surgical device and configuring the generic surgical device with respect to a 3D medical image to select one or more real surgical devices.

FIG. 1 is a flow diagram that illustrates a process of generating a digital 3D representation of a generic surgical device and using the generic surgical device using that representation in pre-operative planning. Step 100 is generating a digital 3D representation of a generic surgical device. The generic surgical device may be representative of a class, sub-class, type, or sub-type of surgical devices. For example, and without limitation, a single generic vascular stent may be representative of all vascular stents, or certain sub-types or sub-classes of vascular stents. Step 102 is moving the digital 3D representation of the generic surgical device into a 3D medical image that includes an anatomic feature of interest. Step 104 is aligning the digital 3D representation of the generic surgical device with the anatomic feature of interest. The anatomic feature of interest may be rendered in isolation or within the 3D medical image. Step 106 is configuring the representation of the generic surgical device relative to the anatomic feature of interest, e.g. adjusting one or more of the size, shape, and material properties of the generic surgical device based on characteristics of the anatomic feature. The result is a configured generic surgical device that represents a desired surgical device for achieving an optimal surgical outcome. Step 108 is determining and selecting one or more optimally matching real surgical devices, e.g. surgical devices that are currently available from medical equipment manufacturers and are closest matches in shape, size, and material to the configured generic surgical device. Step 110 is replacing the 3D representation of the configured generic surgical device with a 3D representation of one or more selected closest-matching real surgical devices. Step 112 is optimizing visualization (e.g., adjust transparency), making one or more final selections of the real surgical devices, and performing pre-operative planning with added annotations. Step 114 is generating a pre-operative surgical planning report, obtaining the selected real surgical devices, and performing surgery with the ability to reference this surgical pre-operative planning report during surgery as needed.

Figure 2:
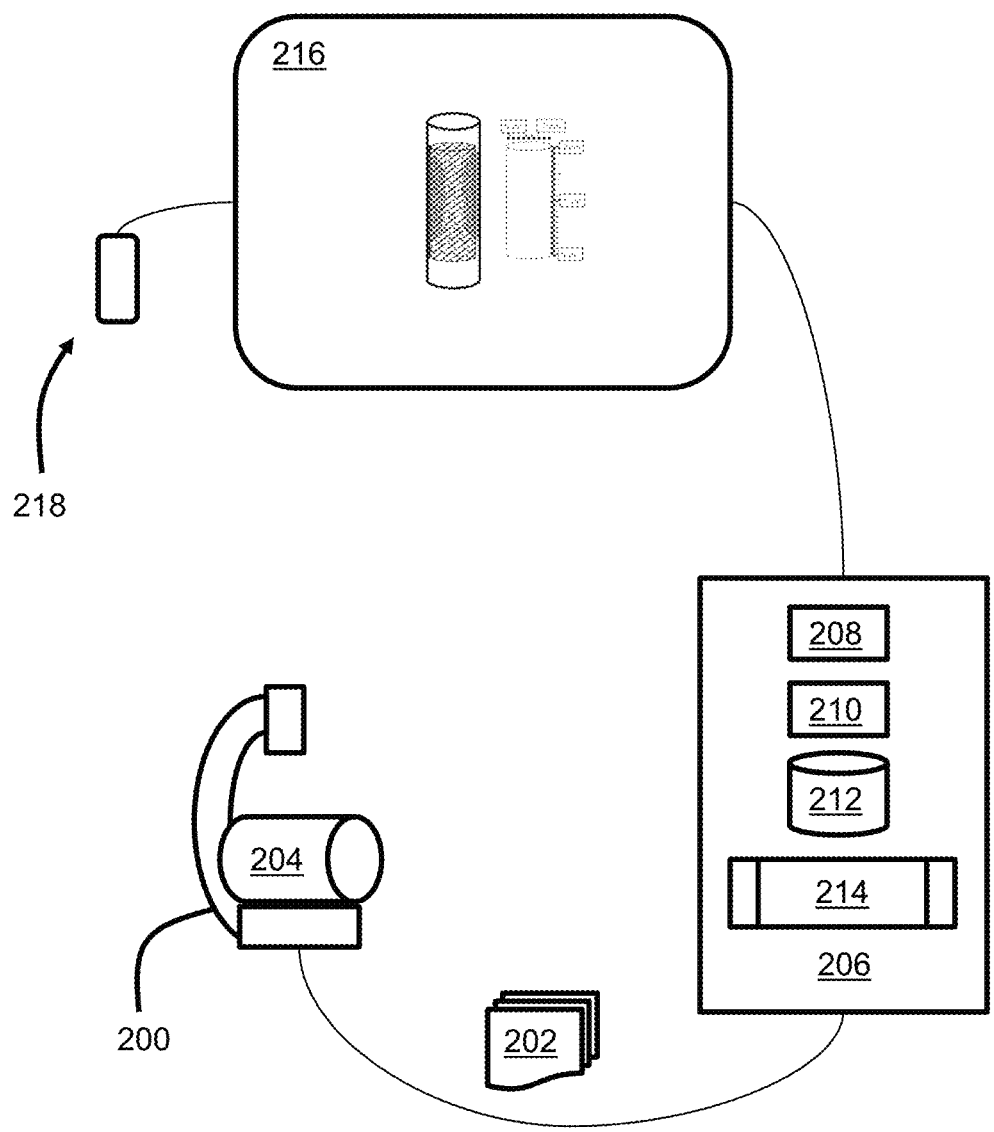
FIG. 2 illustrates an apparatus for implementing the process of FIG. 1.

FIG. 2 illustrates an apparatus for implementing the process illustrated in FIG. 1. A radiologic imaging system 200 (e.g., X-ray, ultrasound, CT (computed Tomography), PET (Positron Emission Tomography), or MRI (Magnetic Resonance Imaging)) is used to generate 2D medical images 202 of an anatomic structure 204 of interest. The 2D medical images 202 are provided to an image processor 206, that includes processors 208 (e.g., CPUs and GPUs), volatile memory 210 (e.g., RAM), and non-volatile storage 212 (e.g. HDDs and SSDs). A program 214 running on the image processor implements one or more of the steps described in FIG. 1. 3D medical images are generated from the 2D medical images and displayed on an IO device 216. The IO device may include a virtual or augmented reality headset, monitor, tablet computer, PDA (personal digital assistant), mobile phone, or any of a wide variety of devices, either alone or in combination. The IO device may include a touchscreen, and may accept input from external devices (represented by 218) such as a keyboard, mouse, and any of a wide variety of equipment for receiving various inputs. However, some or all the inputs could be automated, e.g. by the program 214.

FIGS. 3A, 3B, 3C, 3D, and 3E collectively illustrate using the IO device and image processor to move, align, and size a representation of a generic surgical device 300 relative to an anatomic structure 302 of interest within a 3D medical image to generate a configured generic surgical device to aid in selection of a real surgical device. FIG. 3A illustrates a 3D digital representation of the generic surgical device 300. The representation of the generic surgical device is rendered on the IO device based on information stored in the image processor, e.g. a database of generic surgical devices in non-volatile storage. The specific generic surgical device 300 in the depicted example is a vascular stent. FIG. 3B illustrates a 3D radiological image of the anatomic structure 302 of interest, which is generated from the 2D medical images provided by the radiologic imaging system to the image processor. In the depicted example the anatomic structure 302 is an artery that is partially filled with atherosclerotic plaque 304. The artery is shown with all other tissues from the 3D medical image subtracted, which is done by the image processor in response to user input. However, the artery could be viewed with the surrounding tissue. FIG. 3C illustrates a 3D digital representation of the generic surgical device 300 being integrated with the 3D radiologic image of the anatomic structure 302 in response to user-input. The 3D representation of the generic surgical device and the 3D radiologic image of the anatomic structure are rendered together on the IO device. The user may select and move the representation of the generic surgical device representation into proximity with the anatomic structure image. FIG. 3D illustrates adjustment of the orientation of the 3D digital representation of the generic surgical device 300 to align with the anatomic structure 302 in response to user input. In the specifically illustrated example, the stent is rotated to align with the artery. However, adjustment of orientation is not limited to rotational movement, and could include, but is not limited to, any combination of X-axis movement, Y-axis movement, Z-axis movement, rotation relative to a point (e.g. center or salient feature), and rotation relative to an axis (e.g., spinning relative to a major axis of the surgical device). FIG. 3E illustrates adjustment of the size of the 3D digital representation of the generic surgical device in response to user input. Specifically, the diameter of the generic stent is adjusted to match the inner diameter of the artery in the illustrated example. Other dimensions could be re-sized, including but not limited to length, width, and depth. Moreover, size adjustments may include length, width, and depth adjustments. One or more portions of the representation of the generic surgical device may be independently oriented and size-adjusted if corresponding real surgical devices are available in such configurations. As will be explained in greater detail below, after configuring the representation of the generic surgical device 300 as described above, the resulting representation of a configured generic surgical device 306 may serve as a model with which to select a real surgical device.

FIGS. 4A, 4B, and 4C collectively illustrate how a surgeon or other medical professional can use the IO device and image processor to select one or more real surgical devices. The image processor may include a database of real surgical devices in non-volatile storage. Real surgical device specifications, including the precise sizes and shapes that are closest matches relative to the configured generic surgical device 306 (FIG. 3E), are presented on the IO device for consideration. More specifically, the representations of real surgical devices that are available from one or more manufacturers are integrated with the image of the anatomic feature of interest. FIG. 4A illustrates representations of three real surgical devices 400, 402, 404 that are closest matches to the configured generic surgical device 306 (FIG. 3E). The real surgical devices 400, 402, 404 are characterized by different sizes, e.g. length, diameter, etc. Real surgical device specifications, including the precise sizes and shapes that are available from a manufacturer, would be uploaded into a digital file. This file would be used to generate a 3D image on the IO device of each real stent selected by the user or image processor for consideration in accordance with Douglas et al. U.S. Pat. No. 8,384,771, which is incorporated by reference. The one or more real surgical devices that are closest matches relative to the configured generic surgical device 306 (FIG. 3E) may be presented on the IO device for consideration and possible selection. More specifically, the representations of the available closest matching real surgical devices may be identified by the program running on the image processor and rendered on the IO device for possible selection. However, identification of matching real surgical devices may also, or alternatively, be manual. FIG. 4B illustrates the anatomic structure 302, which is a blood vessel (e.g., coronary artery) partially filled with atherosclerotic plaque in the depicted example. The anatomic structure has been segmented-out so that all tissues other than the coronary artery, which is the tissue of interest, have been subtracted from the 3D medical image. This is performed in accordance with Douglas et al, U.S. Pat. No. 8,384,771, which is incorporated by reference. Either or both the anatomic structure and real surgical devices may be reoriented for common alignment. FIG. 4C illustrates the representations of the three real surgical devices 400, 402, 404 superimposed on separate representations of the anatomic structure 302. The real surgical devices and anatomic structure representations are rendered at the same scale so it can be readily determined from visual inspection that the top stent (real surgical device 400) has too large of a diameter for the blood vessel, the middle stent (real surgical device 402) is appropriately sized for the blood vessel, and the bottom stent (real surgical device 404) has too small of a diameter for the blood vessel. Consequently, the middle stent (real surgical device 402) may be selected for the pre-operative plan.

Figure 5:
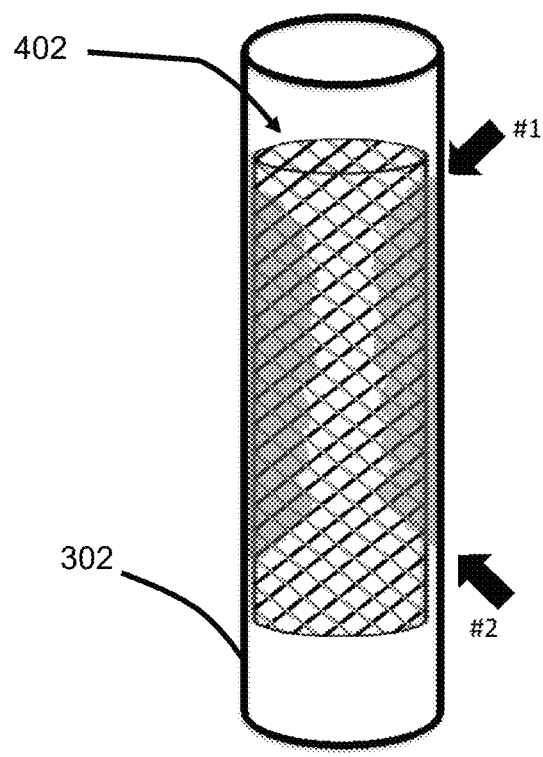
FIG. 5 illustrates adding annotations in the pre-operative planning phase.

FIG. 5 illustrates the ability for the surgeon or other medical professional to use the IO device and image processor to add annotations in the pre-operative planning phase. The illustrated example includes multiple annotations #1, #2, associated with an image including the representation of the anatomic feature 302 and the selected real surgical device 402. The annotations may mark notes to the surgeon or other medical professional regarding key findings on the image or surgical device or how they interact. The annotations may include descriptive text, reference characters, or both. Descriptions 504, 506 associated respectively with the annotations #1, #2 can be filed in the surgical report below. Moreover, the annotations may include hyperlinks to the descriptions, e.g. selecting annotation #1 may cause the associated description 504 to automatically be presented on the IO device.

FIGS. 6A, 6B, and 6C collectively illustrate the ability for the surgeon or other medical professional to use the IO device and image processors to adjust the transparency of a representation of a surgical device 600, which may be real or generic, and/or anatomic feature 302, such that visualization is optimized and pre-operative planning is optimized. FIG. 6A illustrates the surgical device 600 (in this case, a vascular stent) partially hidden behind atherosclerotic vascular calcifications 604. FIG. 6B illustrates the atherosclerotic vascular calcifications hidden behind the surgical device 600. FIG. 6C illustrates the transparent appearance of the surgical device 600 and atherosclerotic vascular calcifications 604, such that both can be visualized.

Figure 7:
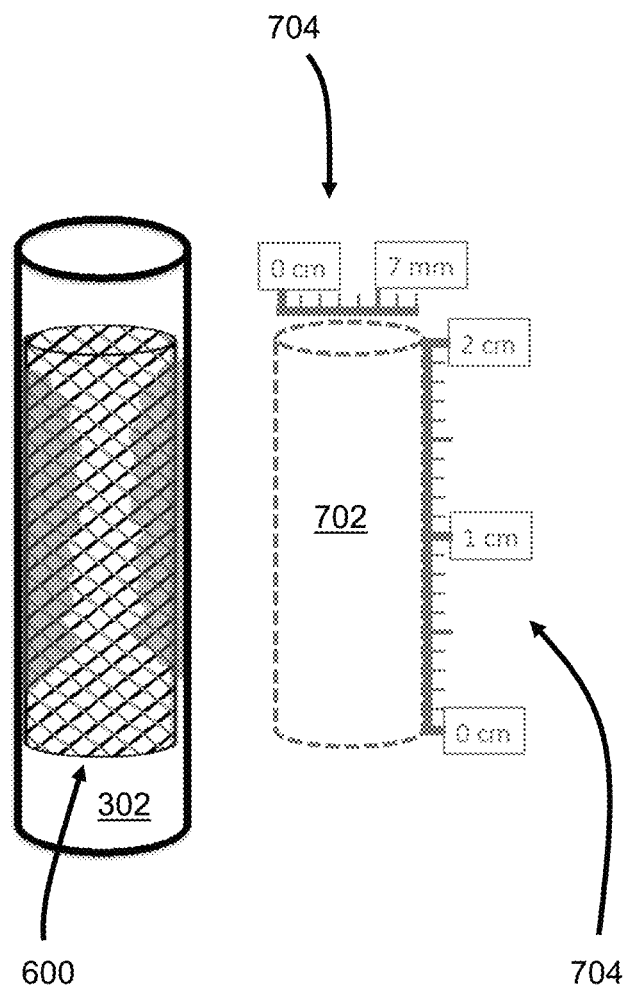
FIG. 7 illustrates associating measurement markers with the representation of the surgical device.

FIG. 7 illustrates the ability for the surgeon or other medical professional to use the IO device and image processor to associate measurements with the surgical device 600. The measurements may be overlaid on the representation of the surgical device (and anatomic feature 302) or presented adjacent to the surgical device, e.g. with a ghost image 702. The measurements may be helpful for identifying optimal size, shape, and/or material for selection of the real surgical device. Measurement markers 704, which in this case show that the stent is 7 mm in diameter and 2 cm in length, quantify the measurements in increments as calculated or stored by the image processor.

Figure 8:
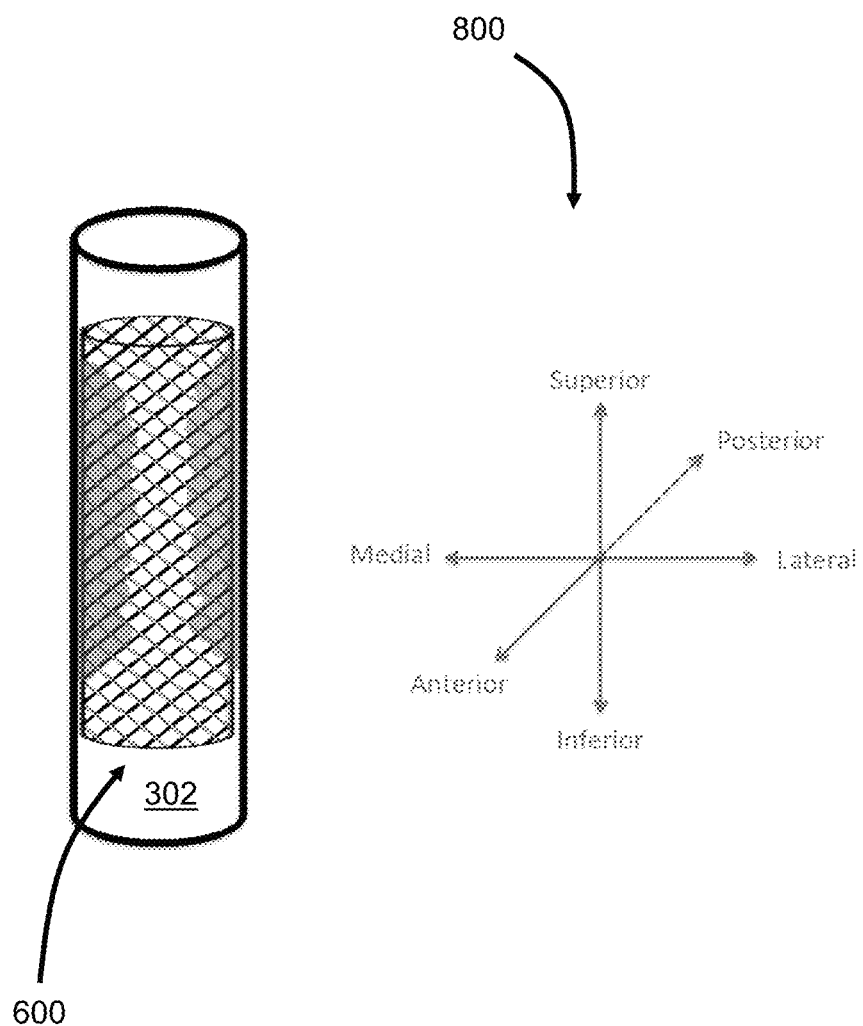
FIG. 8 illustrates associating location indicators with the representation of the surgical device.

FIG. 8 illustrates the ability for the surgeon or other medical professional to use the IO device and image processor to add location indicators 800 to the representation of the surgical device 600 and anatomic feature 302. The location indicators may be overlaid on the surgical device or presented adjacent to the surgical device to optimize visualization and pre-operative planning. The location indicators shown provide directional information including: superior, inferior, anterior, posterior, medial, and lateral.

Figure 9:
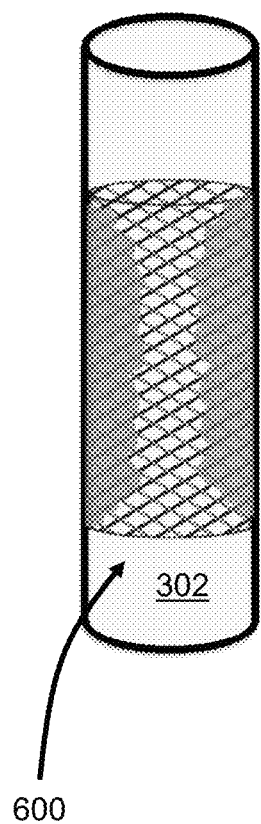
FIG. 9 illustrates adding false color to the surgical device.

FIG. 9 illustrates the ability for the surgeon or other medical professional to use the IO device and image processor to add false color to the representation of the surgical device 600 to optimize visualization and pre-operative planning. In this case, false color is added to the stent, which is colored blue, which can help aid in visualization where the representation of the surgical device is integrated with the image of the anatomic feature 302.

Figure 10:
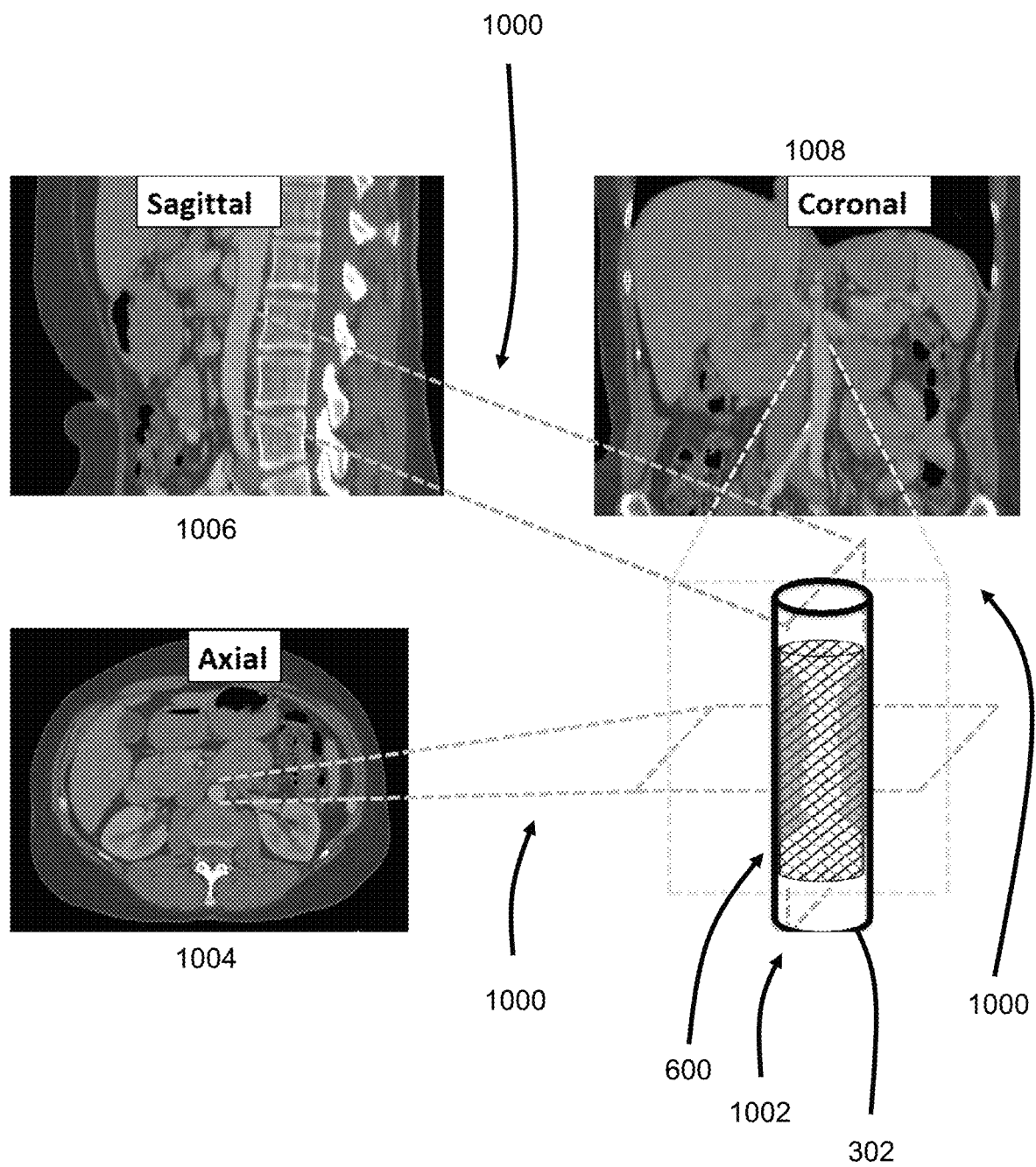
FIG. 10 illustrates associating reference lines with a 3D image that includes both the digital 3D representation of the surgical device and the 3D medical image, where the reference lines are associated with conventional cross-sectional imaging planes, such as axial, sagittal, coronal or oblique imaging.

FIG. 10 illustrates the ability for the surgeon or other medical professional to use the IO device and image processor to add reference lines 1000 from a 3D image 1002, which includes both the digital 3D representation of surgical device 600 and the anatomic feature 302, to conventional cross-sectional imaging planes, such as axial 1004, sagittal 1006, and coronal or oblique 1008. Note that the yellow lines are reference from the stent to the coronal plane image. The pink lines are reference lines from the stent to the sagittal image. The blue lines are reference lines from the stent to the axial image.

Figure 11:
FIG. 11 illustrates generating a pre-surgical planning report to document surgical device selection and key pre-operative annotations identified during the planning for reference during surgery.

FIG. 11 illustrates the ability for the surgeon or other medical professional to use the IO device and image processor to generate a pre-surgical planning report 1100 to document real surgical device selection and key pre-operative annotations identified during the planning for reference during surgery. This is a sample pre-operative planning report, which includes the following sections: patient identifying information, clinical history, comparisons, radiology report findings, surgical anatomy description, surgical device selection, landmarks uploaded, conclusions, recommendations. Key information from the added quantitative analysis that can be performed with the 3D cursor can be included in the radiology reports. Furthermore, follow up reports can include current and prior exams with quantitative analysis and analysis on how the lesion has changed over time.

Figure 12:
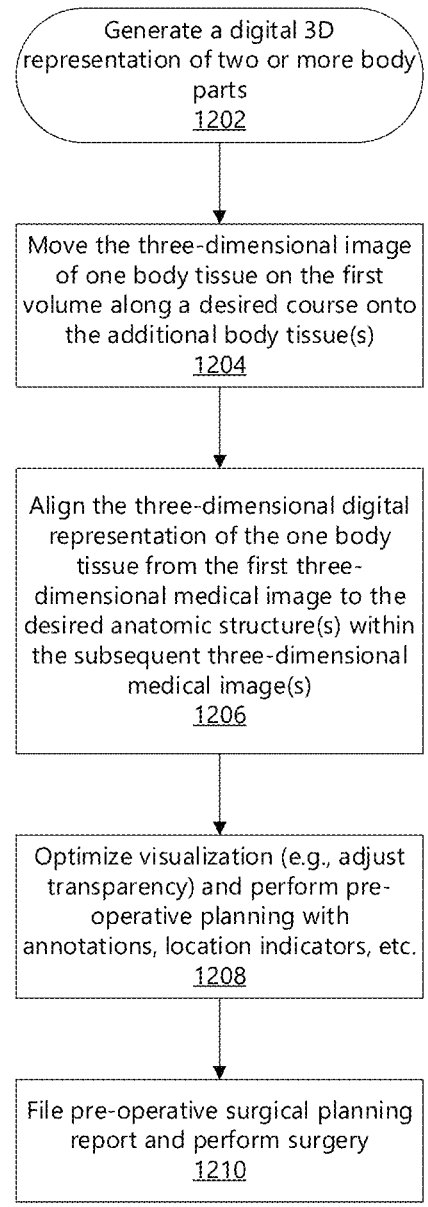
FIG. 12 is a flow diagram that illustrates moving one volume of body tissue over another volume of body tissue for pre-operative planning or diagnosis processes.

FIG. 12 is a flow diagram that illustrates using the image processor and TO device to virtually move one volume of body tissue with respect to another volume of body tissue for pre-operative planning or diagnosis processes. The steps may be performed by the program running on the image processor. Step 1202 is to generate digital 3D representations of two or more anatomic features. Step 1204 is to move the representation of one anatomic feature on the first volume along a desired course relative to the representation of the other anatomic feature, e.g. until overlaid or superimposed. Step 1206 is to align the 3D digital representations of the anatomic features with respect to one-another, e.g. of the one body tissue from the first 3D medical image to the desired anatomic structure(s) within the subsequent 3D medical image(s). Step 1208 is to optimize visualization (e.g., adjust transparency) and perform pre-operative planning with annotations, location indicators, etc. Step 1210 is to file a pre-operative surgical planning report and perform surgery with the ability to reference the pre-operative surgical planning report as needed during the surgery.

Figure 13:
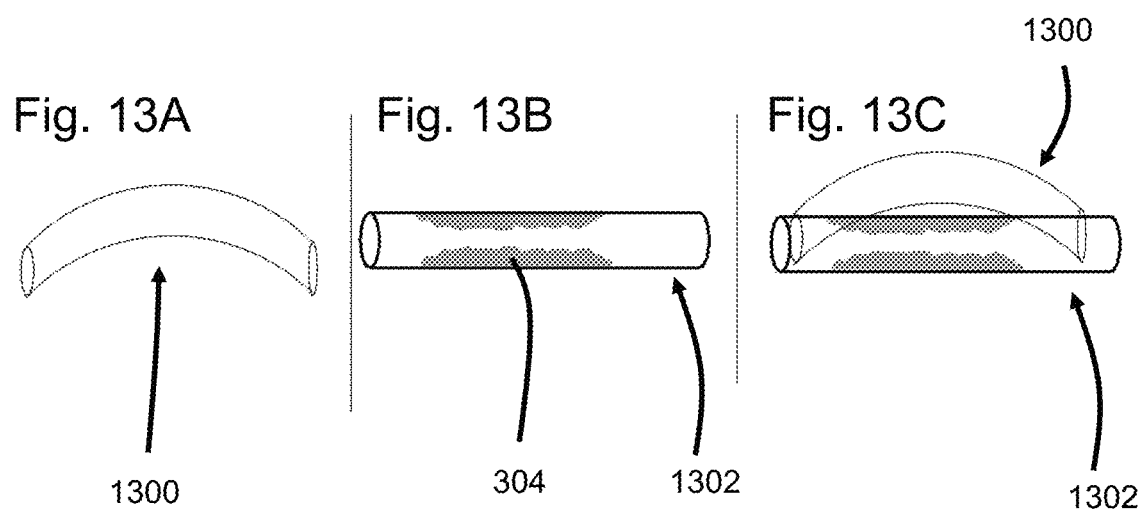
FIGS. 13A, 13B, and 13C collectively illustrate clipping a representation of tissue and virtually moving it to a different area of the body for pre-operative planning.

FIGS. 13A, 13B, and 13C collectively illustrate the ability for the surgeon or other medical professional to use the IO device and image processor to virtually clip (e.g., resect or excise) one tissue and move it to a different area of the body for pre-operative planning in accordance with the process of FIG. 12. FIG. 13A depicts an anatomic feature 1300 to be grafted, e.g. a vein of the leg. The anatomic feature 1300 to be grafted is imaged pre-operatively and segmented-out so that all other tissues are subtracted. This is performed in accordance with Douglas et al, U.S. Pat. No. 8,384,771. FIG. 13B depicts an anatomic feature 1302 being clipped. Specifically, a coronary artery that is partially filled with atherosclerotic plaque 304 is shown. The image of anatomic feature 1302 has also been segmented-out so that all tissues other than the coronary artery, which is the tissue of interest, are subtracted. This is performed in accordance with Douglas et al, U.S. Pat. No. 8,384,771. FIG. 13C depicts both anatomic features 1300, 1302 superimposed on one another with all other tissues subtracted. The various aspects already described above regarding surgical devices could be implemented with the anatomic features. Thus, suitability of the anatomic feature to be grafted can be determined through visual comparison with the anatomic feature to be clipped.

CLAIMS

Several features, aspects, embodiments, and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method comprising:
performing segmentation of a volume at a first time point to define a structure wherein the structure at the first time point has a first size, a first shape and contains a first salient feature;
performing filtering of the volume at the first time point wherein portions of the volume at the first time point not pertaining to the structure at the first time point are removed;
performing segmentation of a volume at a second time point to define a structure wherein the structure at the second time point has a second size, a second shape and contains a second salient feature wherein the second salient feature corresponds to the first salient feature of the structure at the first time point;
performing filtering of the volume at the second time point wherein portions of the volume at the second time point not pertaining to the structure at the second time point are removed;
superimposing the structure at the first time point with the structure at the second time point comprising:
responsive to a first user input, moving the first salient feature of the structure at the first time point relative to the second salient feature of the structure at the second time point such that the first salient feature of the structure at the first time point is superimposed on the second salient feature of the structure at the second time point; and
responsive to a second user input, aligning the first salient feature of the structure at the first time point relative to the second salient feature of the structure at the second time point such that the orientation of the structure at the first time point matches the orientation of the structure at the second time point; and
responsive to a third user input, displaying the structure at the first time point transparently and the structure at the second time point non-transparently in a superimposed fashion, wherein the structure at the first time point and the structure at the second time point relate to human body parts.

2. The method of claim 1 wherein a user assesses interval changes of one of the group consisting of:
the first size of the structure at the first time point compared with the second size of the structure at the second time point; and
the first shape of the structure at the first time point compared with the second shape of the structure at the second time point.

3. The method of claim 1 further comprising: moving the structure at the first time point such that the first salient feature of the structure at the first time point is not superimposed on the second salient feature of the structure at the second time point.

4. The method of claim 3 further comprising: displaying the structure at the first time point adjacent to the structure at the second time point.

5. The method of claim 1 further comprising replacing voxels from the structure at the first time point that overlap with voxels from the structure at the second time point.

6. The method of claim 1 comprising displaying the structure at the first time point and the structure at the second time point on an augmented reality display.

7. The method of claim 1 comprising displaying the structure at the first time point and the structure at the second time point on a virtual reality display.

8. The method of claim 1 comprising displaying the structure at the first time point and the structure at the second time point on a monitor.

9. An apparatus comprising:
an IO device; and
an image processor in communication with the IO device, the image processors comprising a program stored on computer-readable non-transitory media, the program comprising:
instructions that perform segmentation of a volume at a first time point to define a structure wherein the structure at the first time point has a first size, a first shape and contains a first salient feature;
instructions that perform filtering of the volume at the first time point wherein portions of the volume at the first time point not pertaining to the structure at the first time point are removed;
instructions that perform segmentation of a volume at a second time point to define a structure wherein the structure at the second time point has a second size, second shape and contains a second salient feature wherein the second salient feature corresponds to the first salient feature of the structure at the first time point;
instructions that perform filtering of the volume at the second time point wherein portions of the volume at the second time point not pertaining to the structure at the second time point are removed:

instructions that superimpose the structure at the first time point with the structure at the second time point comprising:

responsive to a first user input, moving the first salient feature of the structure at the first time point relative to the second salient feature of the structure at the second time point such that the first salient feature of the structure at the first time point is superimposed on the second salient feature of the structure at the second time point; and responsive to a second user input, aligning the first salient feature of the structure at the first time point relative to the second salient feature of the structure at the second time point such that the orientation of the structure at the first time point matches the orientation of the structure at the second time point; and instructions that responsive to a third user input, display the structure at the first time point transparently and the structure at the second time point non-transparently in a superimposed fashion, wherein the structure at the first time point and the structure at the second time point relate to human body parts.

10. The apparatus of claim 9 wherein the instructions provide capability for a user to assess interval changes of one of the group consisting of:

the first size of the structure at the first time point compared with the second size of the structure at the second time point; and the first shape of the structure at the first time point compared with the second shape of the structure at the second time point.

11. The apparatus of claim 9 comprising instructions that move the structure at the first time point such that the first salient feature of the structure at the first time point is not superimposed on the second salient feature of the structure at the second time point.

12. The apparatus of claim 11 comprising instructions that display the structure at the first time point adjacent to the structure at the second time point.

13. The apparatus of claim 9 further comprising instructions that replace voxels from the structure at the first time point that overlap with voxels from the structure at the second time point.

14. The apparatus of claim 9 comprising instructions that display the structure at the first time point and the structure at the second time point on an augmented reality display.

15. The apparatus of claim 9 comprising displaying the structure at the first time point and the structure at the second time point on a virtual reality display.

16. The apparatus of claim 9 comprising displaying the structure at the first time point and the structure at the second time point on a monitor.

* * * * *